US011612305B1

(12) United States Patent
Lee

(10) Patent No.: US 11,612,305 B1
(45) Date of Patent: Mar. 28, 2023

(54) RECEPTACLE FOR A LARYNGOSCOPE AND METHOD OF USING SAME

(71) Applicant: HyunSuk Lee, Guilford, CT (US)

(72) Inventor: HyunSuk Lee, Guilford, CT (US)

(*) Notice: Subject to any disclaimer, the term of this patent is extended or adjusted under 35 U.S.C. 154(b) by 0 days.

(21) Appl. No.: 14/732,125

(22) Filed: Jun. 5, 2015

Related U.S. Application Data

(60) Provisional application No. 62/008,607, filed on Jun. 6, 2014.

(51) Int. Cl.
*A61B 1/00* (2006.01)
*A61B 1/267* (2006.01)

(52) U.S. Cl.
CPC .......... *A61B 1/00144* (2013.01); *A61B 1/267* (2013.01)

(58) Field of Classification Search
CPC ................................. A61B 1/00144
See application file for complete search history.

(56) References Cited

U.S. PATENT DOCUMENTS

| 3,189,252 | A | * | 6/1965 | Miller | B65D 31/145 383/57 |
| 4,834,077 | A | * | 5/1989 | Sun | A61B 1/267 600/194 |
| 4,896,773 | A | | 1/1990 | Zilio | |
| 4,898,477 | A | | 2/1990 | Cox et al. | |
| 4,911,560 | A | * | 3/1990 | Hoover | B65D 33/007 383/35 |
| 5,174,658 | A | | 12/1992 | Cook et al. | |
| 5,184,896 | A | | 2/1993 | Hammond et al. | |
| 5,549,388 | A | * | 8/1996 | Wilkes | A61B 50/30 383/120 |
| 5,647,670 | A | | 7/1997 | Iscovich | |
| 5,970,979 | A | * | 10/1999 | Christofel | A61B 46/00 128/853 |
| 6,206,889 | B1 | | 3/2001 | Bennardo | |
| 6,308,875 | B1 | | 10/2001 | Almo | |
| 6,543,642 | B1 | | 4/2003 | Milliorn | |
| 6,561,963 | B2 | | 5/2003 | Totani | |
| 6,800,051 | B2 | * | 10/2004 | Koehn | B31B 70/00 493/227 |
| 6,899,460 | B2 | | 5/2005 | Turvey et al. | |

(Continued)

FOREIGN PATENT DOCUMENTS

| EP | 494413 A2 * | 7/1992 | ............. A61B 46/00 |
| GB | 1348547 | 3/1974 | |
| JP | 2004000447 | 1/2004 | |

OTHER PUBLICATIONS

"BeeSafe Honeycomb Padding"; Cygnus Medical; 1 page; http://www.cygnusmedical.com/products_new/beesafe.html; Accessed: Sep. 7, 2021.

(Continued)

*Primary Examiner* — Julianna N Harvey
(74) *Attorney, Agent, or Firm* — Cantor Colburn LLP

(57) ABSTRACT

A receptacle for receiving a medical device and a method of making and using the receptacle. The receptacle includes an elongate base, a cover, the cover and elongate base hingedly secured to one another, the cover and the elongate base cooperating to define an envelope having mouth extending into an interior area of the envelope, and a biasing member communicating with the cover and configured to bias the mouth in an open position for receiving the medical device through the mouth into the interior area.

15 Claims, 15 Drawing Sheets

(56) References Cited

U.S. PATENT DOCUMENTS

| | | |
|---|---|---|
| 7,343,919 B2 | 3/2008 | Czajka et al. |
| 7,837,606 B2 | 11/2010 | Tetenborg et al. |
| 8,061,558 B2 | 11/2011 | Jordan et al. |
| 8,104,960 B2 | 1/2012 | Gill et al. |
| 8,292,076 B2 | 10/2012 | Dacey |
| 2002/0168120 A1 | 11/2002 | Wessling et al. |
| 2003/0009858 A1 | 1/2003 | Goldberg et al. |
| 2011/0301459 A1 | 12/2011 | Gharib |
| 2012/0205269 A1 | 8/2012 | Ludvig |
| 2013/0043155 A1 | 2/2013 | Hartley |
| 2014/0161372 A1 | 6/2014 | Sulpizio et al. |
| 2014/0286595 A1 | 9/2014 | Moreschini |

OTHER PUBLICATIONS

"Plasma-Cel Instrument Guards"; Cygnus Medical; 1 page; http://www.cygnusmedical.com/products/plasmacel_page/plasmacel.html; Accessed: Apr. 15, 2021.

\* cited by examiner

RECEPTACLE FOR A LARYNGOSCOPE AND METHOD OF USING SAME

This application claims priority to U.S. provisional patent application Ser. No. 62/008,607 filed Jun. 6, 2014.

BACKGROUND OF THE INVENTION

1. Field of the Invention

The present invention relates to a receptacle for a laryngoscope, oral airway, endotracheal tube (ETT) and the like and a method of using the same. In particular, the invention relates to isolation of clean and contaminated laryngoscopes and other medical equipment and disposal of medical waste.

2. Description of Related Art

Cleanliness and even sterility is desired in many medical settings, such as, for example, patient examination rooms, operating rooms, hospital rooms, procedure rooms, emergency rooms and blood drawing facilities ("labs"). In particular, the sterility and cleanliness of medical devices as well as the cleanliness of the overall environment is required in operating rooms. Many procedures and protocols concerning sterility, cleanliness and maintenance are put into place in hospitals and outpatient facilities that have operating rooms.

Despite these procedures and protocols and the best efforts of the doctors, nurses and other staff members, cleanliness of a medical setting may be compromised when the care of the patient takes priority. For example, a doctor such as an anesthesiologist must simultaneously monitor a patient under anesthesia while properly handling medical devices such as a laryngoscope that come into contact with the patient or the patient's bodily fluids. In some instances, the doctor may sacrifice proper handling of such medical devices in favor of urgent patient care needs. Accordingly, the cleanliness and sterility of the operating room and/or medical devices used in the operating room may be compromised during improper handling of medical equipment and/or improper disposal of medical waste.

For many reasons, including, for example, inadequate training, poor personal habits, carelessness, the need for urgent patient care, or lack of proper equipment, unintended cross-contaminated medical equipment may be used on patients, the patient may be exposed to a contaminated environment, or staff and patients may be exposed to improperly disposed medical equipment. Such contamination and improper disposal and its significance oftentimes goes unnoticed or is ignored.

SUMMARY OF THE INVENTION

What is needed is a system, receptacle and/or process that allows a doctor, nurse or other staff member to, while simultaneously monitoring a patient, enable proper handling and discarding of medical equipment without contaminating the surrounding environment. Additionally, what is also needed is a system, receptacle and/or process that enables a doctor, nurse or other staff member to properly handle clean and soiled medical equipment by making it easier to maintain isolation of a clean (or contaminated) portion of the medical equipment from other medical equipment and/or the environment. The present invention is believed to be an answer to the foregoing needs.

Bearing in mind the problems and deficiencies of the prior art, it is therefore an object of the present invention to provide an improved method, system and device to monitor a patient while simultaneously properly handling and discarding medical equipment without contaminating the surrounding environment.

It is another object of the present invention to provide an improved method, system and device for maintaining cleanliness and sterility of the operating room and/or medical devices used in the operating room that might be compromised during improper handling of medical equipment and/or improper disposal of medical waste.

A further object of the invention is to provide an improved method and system for using a laryngoscope during a medical procedure on a patient.

Still other objects and advantages of the invention will in part be obvious and will in part be apparent from the specification.

The above and other objects, which will be apparent to those skilled in the art, are achieved in the present invention which is directed in one aspect to a method of using a laryngoscope during a medical procedure on a patient comprising providing a laryngoscope handle, providing a blade for attaching to the handle and providing a receptacle for temporary storage of the laryngoscope blade. The receptacle has an exterior exposed to the environment around the patient and a normally open mouth leading to an interior area of the receptacle, the receptacle being disposed on a surface. The method includes attaching the blade to the handle to make the laryngoscope operable, inserting the laryngoscope blade into an oral cavity of the patient, and removing the blade from the oral cavity while maintaining a grip with one hand on the laryngoscope handle. The method further includes, while still maintaining the grip with the one hand on the laryngoscope handle, inserting the blade through the open mouth into the interior of the receptacle, without touching the laryngoscope or the receptacle with another hand and subsequently releasing the one hand from the laryngoscope handle so that the handle stays on the exterior of the receptacle while keeping the blade substantially within the interior of the receptacle. The laryngoscope blade may be stored during the medical procedure in a position isolated from contamination by or contaminating the handle, the surface and the environment around the patient.

The method may further include, after inserting the blade into the receptacle, folding the handle toward the blade while the blade is pushed against the interior surface of the receptacle, during which the blade is prevented from coming in contact with the handle, the operator or the surface on which the receptacle is disposed.

The method may also further include, after inserting the blade into the receptacle, and while still maintaining the grip with the one hand on the laryngoscope handle, folding the handle, toward the blade, against the exterior of the receptacle, without touching the handle against the blade and without touching the laryngoscope with another hand.

The handle may be folded, toward the blade, against the exterior of the receptacle and the blade may rest against the interior of the receptacle, during storage in which the blade is isolated from the handle, operator or the surface.

The handle may be folded toward the blade against the exterior of the receptacle without touching the handle against the surface on which the receptacle is disposed, and during storage the handle may be isolated from contamination by the surface. The blade may remain substantially within the interior of the receptacle during storage and the handle may remain substantially on the exterior of the receptacle during storage.

The laryngoscope may be subsequently reusable during the medical procedure on the patient by unfolding the handle away from the blade and removing the blade from the receptacle.

The receptacle may be disposed on a substantially horizontal surface within an arm's reach of an operator using the laryngoscope while standing or sitting near the patient. An adhesive may be provided to removably secure the receptacle on the surface. The receptacle may comprise a portion of an original packaging of the blade when new.

The method may include inserting the blade into the receptacle with one hand without having the need to hold the receptacle with the other hand or otherwise requiring the use of the other hand in the insertion of the blade into the receptacle. The method may further include using the other hand to hold an endotracheal tube within a trachea of the patient while the one hand inserts the blade into the receptacle and folds the handle toward the blade. The method may further include separating the blade from the handle and disposing of the blade while in the receptacle.

The receptacle may have a base for contact with the surface and an opposite, cover out of contact with the surface, and the base may be longer than the cover at the mouth of the receptacle to provide isolation of the laryngoscope from the surface on which the receptacle is disposed. The receptacle may have a base for contact with the surface and an opposite, cover out of contact with the surface, and the cover may be shorter than the base at the mouth of the receptacle to facilitate insertion of the blade into the interior of the receptacle and isolation of the blade. The receptacle may have a base and a cover over the base, the cover being wider than the base, and/or having folds or pleats in it.

In a further aspect the invention is directed to a receptacle for receiving a medical device, the receptacle comprising: an elongate base; a cover, the cover and elongate base hingedly secured to one another; the cover and the elongate base cooperating to define an envelope having mouth extending into an interior area of the envelope; and a biasing member communicating with the cover and configured to bias the mouth in an open position for receiving at least a portion of the medical device through the mouth into the interior area.

Another aspect of the present invention is directed to a method of isolating at least a portion of a medical device, the method comprising: positioning a receptacle according to any embodiment disclosed herein at a location easily accessible to medical personnel while the medical personnel monitors a patient; utilizing a medical device on the patient; and inserting at least a portion of the medical device utilized on the patient into the receptacle, thereby isolating at least a portion of the medical device.

A further aspect of the present invention is directed to a method of manufacturing a receptacle for receiving a medical device, the method comprising: hingedly securing a cover to an elongate base, the cover and the elongate base cooperating to define an envelope having a mouth extending into an interior area of the envelope; and positioning a biasing member to communicate with the cover and to bias the mouth in an open position for receiving at least a portion of the medical device through the mouth into the interior area.

These and other aspects of the invention are discussed in more detail herein and are illustrated in the attached Figures.

BRIEF DESCRIPTION OF THE DRAWINGS

The features of the invention believed to be novel and the elements characteristic of the invention are set forth with particularity in the appended claims. The figures are for illustration purposes only, are not drawn to scale and are not meant to limit the invention in any way. The invention itself, however, both as to organization and method of operation, may best be understood by reference to the detailed description which follows taken in conjunction with the accompanying drawings in which:

DESCRIPTION OF THE EMBODIMENT(S) OF THE INVENTION

Figure 1:
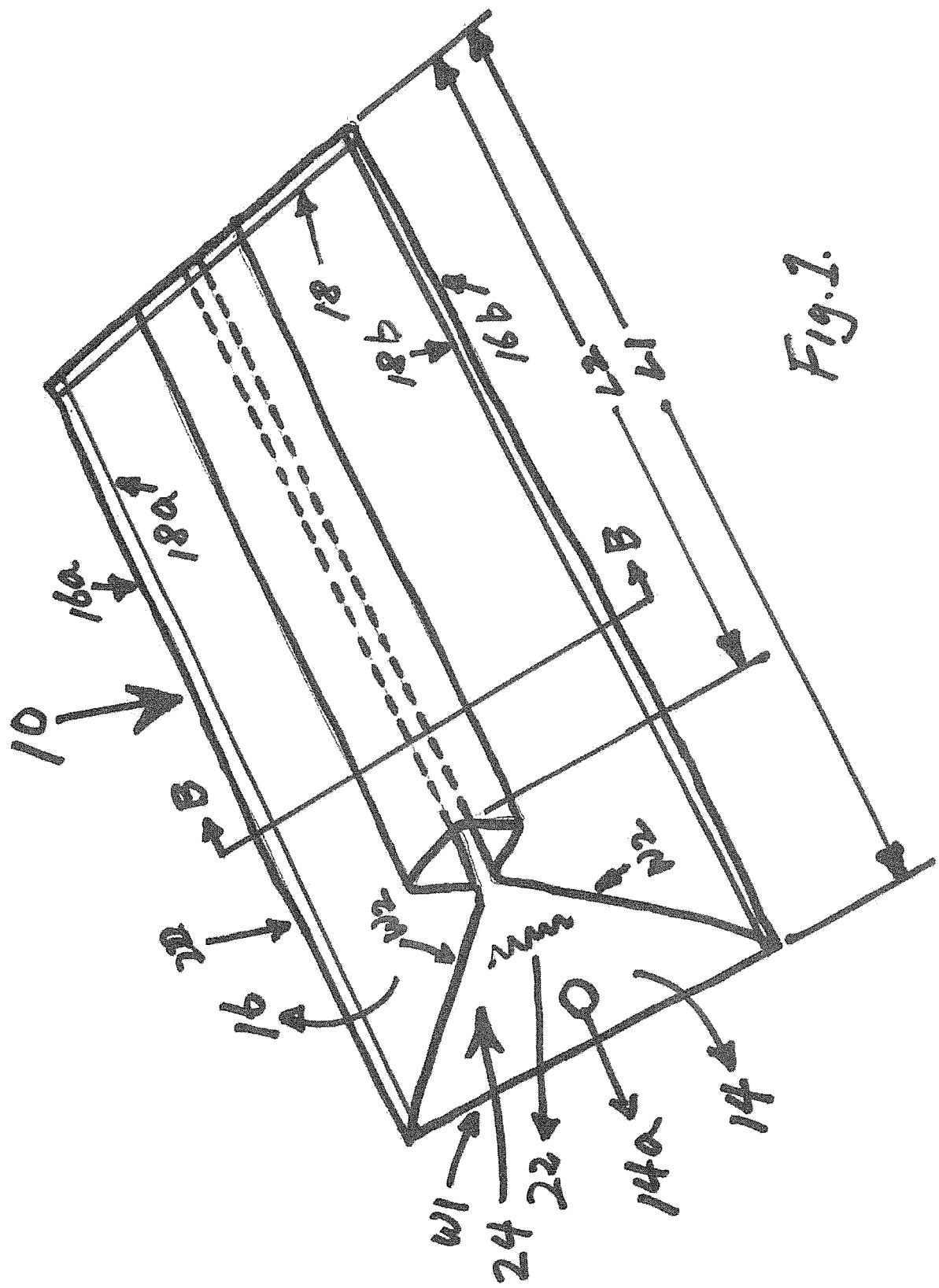
FIG. 1 is a view of a receptacle according to an embodiment discussed herein.

In describing the embodiments of the present invention, reference will be made herein to FIGS. 1-14 of the drawings in which like numerals refer to like features of the invention.

The present invention is directed to a method, a system and/or a device that allows for proper use of clean and contaminated medical devices. The receptacle described herein provides such a device while minimizing distraction of a medical provider from providing patient care. The method of using the receptacle allows easy handling and isolation of clean and contaminated medical devices, thereby reducing the chance of exposing a patient or other devices to contaminated medical devices. The reduction in contamination thus enhances patient care.

FIGS. 1-4 illustrate a receptacle 10 for receiving a medical device 12. The medical device 12 received by the receptacle 10 may be clean or contaminated. If a clean medical device 12 is inserted into the receptacle 10, it is to isolate it from the environment and possible contamination, thereby maintaining the cleanliness of the medical device. If a contaminated medical device is inserted into the receptacle 10, it is to prevent the contamination from spreading to the environment, people near the device, or other medical devices or equipment. It is contemplated that only a portion of the medical device 12 may be inserted into (i.e., received by) the receptacle 10.

A medical device 12 includes medical devices and any other solid material that has, or will, come into contact with a patient (not shown) or has come into contact with bodily fluids of the patient, or has been contaminated in some other manner. Examples of medical devices 12 include, but are not limited to, disposable and non-disposable medical devices used in the intubation, extubation and airway management of patients, cotton, gowns, masks, adhesive tape, bandages, gauze, gloves and the like. It is also contemplated that the medical devices 12 may include biohazard materials such as material, e.g., airway devices, gauze, bandages, gloves, gowns, cotton, that is saturated in blood or a bodily secretion. Should biohazard materials be disposed of in the receptacle 10, the receptacle must be disposed of according to proper biohazard disposal procedures.

The receptacle 10 includes an elongate base 14 and a cover 16. The cover 16 and the elongate base 14 are hingedly secured to one another. In one embodiment, the elongate base 14 and the cover 16 are made from a polymeric material such as, for example, polyvinyl chloride (PVC), polyester, polypropylene, polyethylene or a combination thereof. It is contemplated that the elongate base 14 may be made of the same or different polymeric material as the cover 16. The polymeric material used to form the elongate base 14 and the cover 16 may be of any color and may be either translucent or opaque. It is contemplated that the polymeric material can be of any thickness desired by the user, for example, a flexible film of about 2 mm in thickness.

While polymeric materials are discussed herein, it is also contemplated that other materials may be utilized to make one or more of the elongate base 14 and the cover 16, including, but not limited to, fabric such as canvas or denim, nylon, cardboard, and the like. For example, in one embodiment, the elongate base 14 may be made of cardboard while the cover may be made of a polymeric material. It is also contemplated that the elongate base 14 and the cover 16 are an integral flexible tube.

Figure 2:
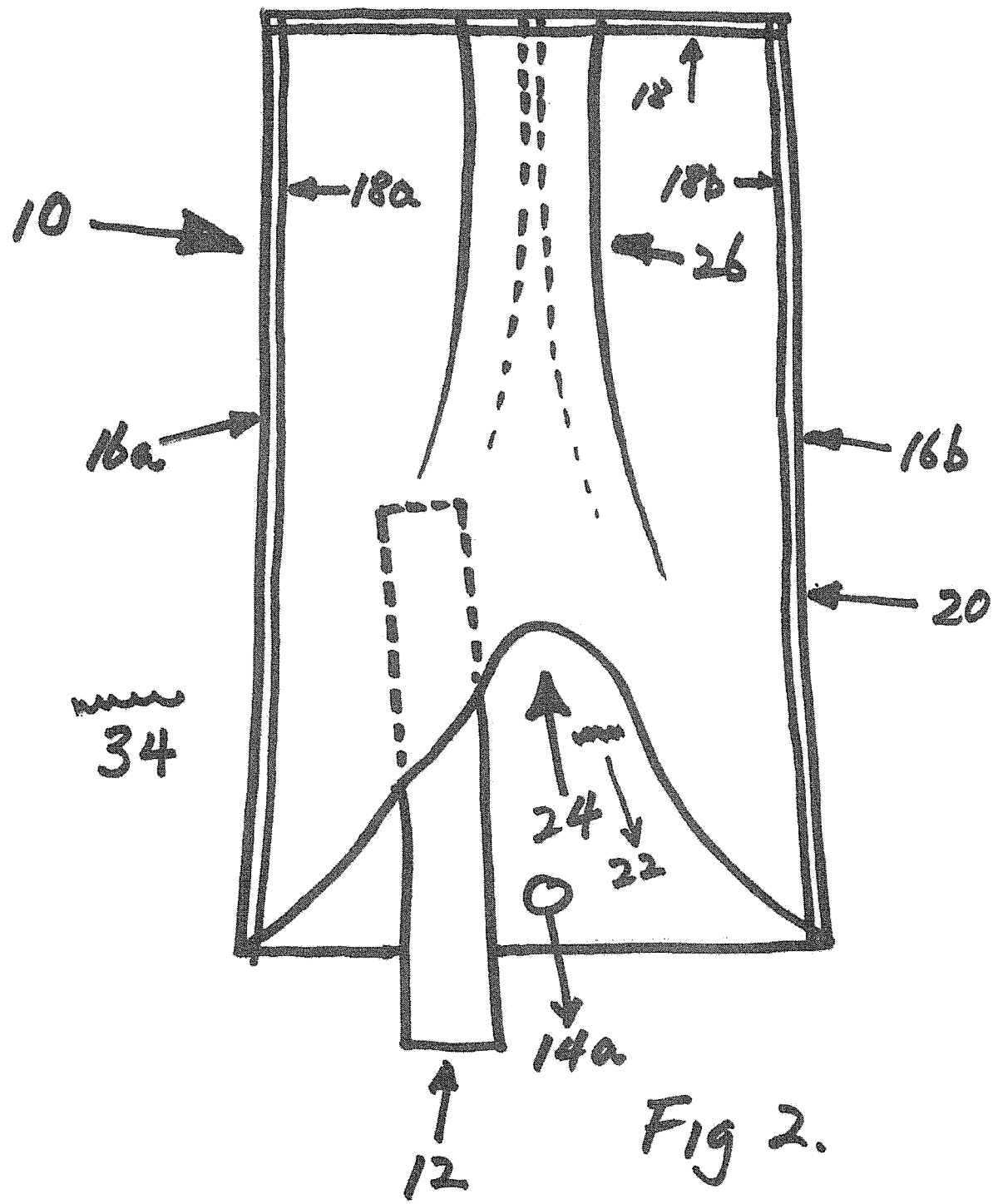
FIG. 2 is a front view of the receptacle illustrated in FIG. 1.

As best shown in FIGS. 1 and 2, the cover 16 and the elongate base 14 are hingedly secured to one another by a seam 18 therebetween. The seam 18 can be a result of a heat seal if the cover 16 and elongate base 14 are made from a polymeric material. If at least one of the cover 16 and the elongate base 14 are made from a material other than a polymeric material, the seam 18 may be made from an adhesive material, sewn stitches or another sealing means known in the art. As shown in FIGS. 1 and 2, the elongate base 14 and the cover 16 may also be hingedly secured to one another by a second seam 18a along a first edge 16a of the cover 16 and a third seam 18b along a second edge 16b of the cover.

The cover 16 and the elongate base 14 cooperate to define an envelope 20 having mouth 22 extending into an interior area 24 of the envelope. As shown in FIGS. 1 and 2, the cover 16 and the elongate base 14 include several seams 18, 18a and 18b to define the envelope 20. As best illustrated in FIG. 1, in one embodiment, the mouth 22 has a V-shaped configuration; however, the receptacle 10 is not limited in this regard as the mouth can have other configurations desired by a user, such as, for example, a square-shaped configuration, a semi-circular-shaped configuration, oblong opening, rectangle, multi-segmented, straight, or the like. The length L2 of cover 16 is shorter than the length L1 of base 14 at mouth 22, so that when the cover is flattened against the base, a portion of the upwardly facing inner base surface 14a at mouth 22 is exposed vertically upward.

The receptacle 10 may also include a biasing member communicating with the cover 16. The biasing member is configured to bias the mouth 22 in an open position for receiving the medical device 12 through the mouth into the interior area 24. In one embodiment, as illustrated in FIGS. 1 and 2, the biasing member is defined by a fold 26 in the cover 16. The fold 26 is positioned between a first edge 16a of the cover 16 and a second edge 16b of the cover. While FIG. 1 illustrates the fold 26 as being positioned roughly equidistant between the first edge 16a and the second edge 16b, the fold may be positioned at any location on the cover 16 between the first edge and the second edge.

While not illustrated herein, it is contemplated that the biasing member may be defined by more than one fold 26 in the cover. The at least one fold 26 is secured in the seam 18 and fans progressively outward toward the mouth 22. While the fold is shown between a first edge 16a of the cover 16 and the second edge 16b of the cover, it is contemplated that the elongate base may also have one or more folds. Further it is contemplated that the biasing member may also be one or more folds in the cover 16 together with one or more folds in the elongate base 14.

Figure 3:
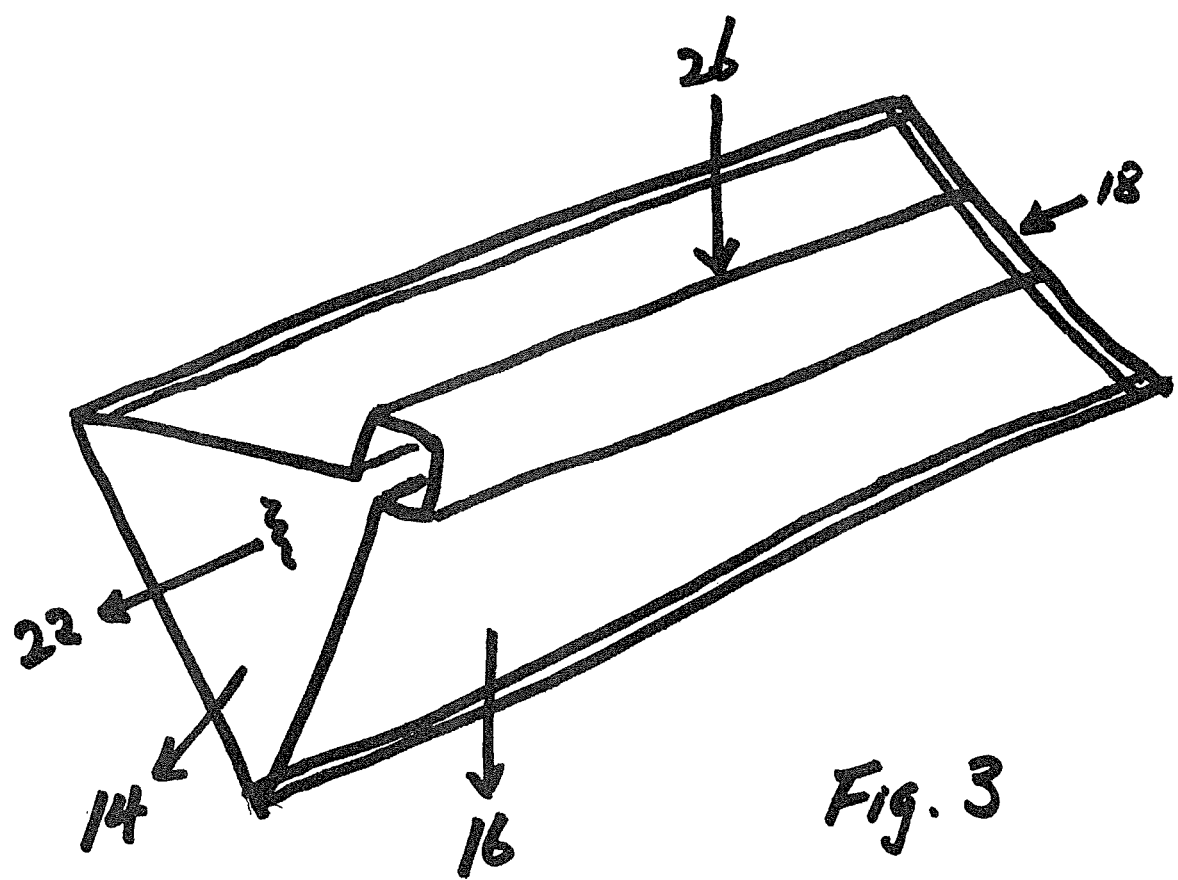
FIG. 3 is a perspective view of a receptacle prior to use.
Figure 4:
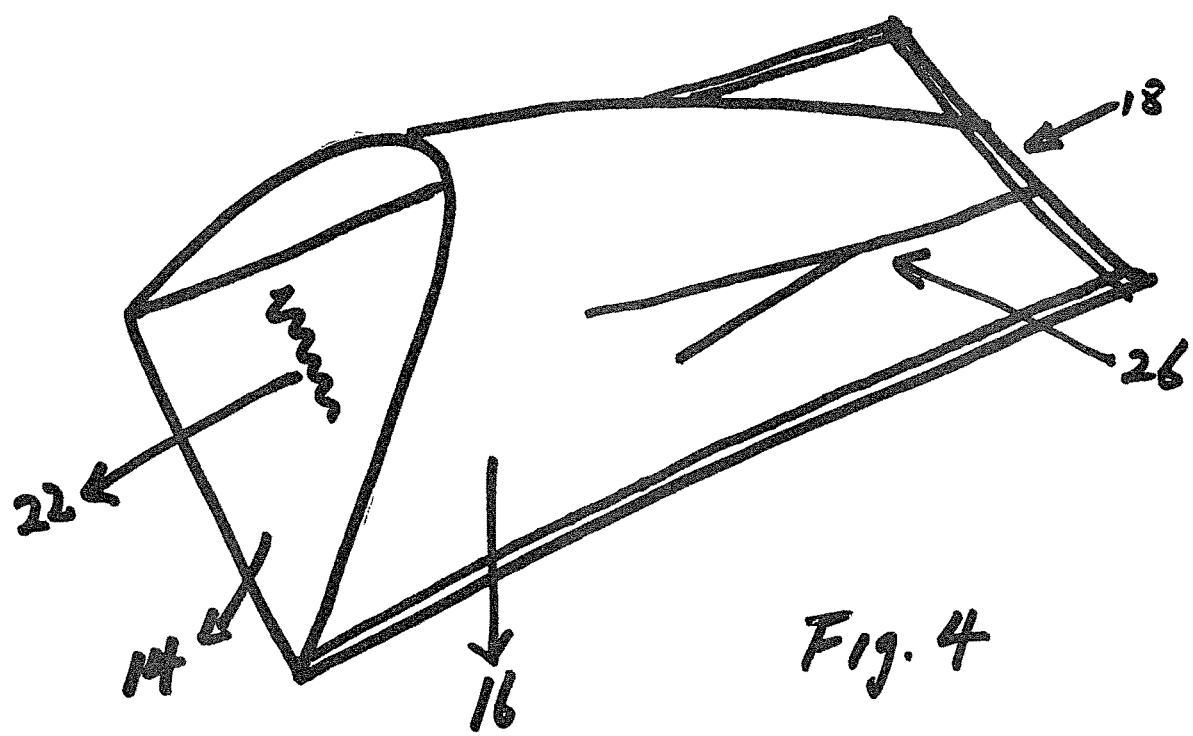
FIG. 4 is a perspective view of the receptacle illustrated in FIG. 10, the receptacle deployed for use.

It is contemplated that if the biasing member is a fold 26 (on either or both the cover 16 and the elongate base 14), the receptacle 10 is able to be stored in a substantially flat configuration as shown in FIG. 3. After deployment of the receptacle 10, i.e., removal from storage for use, the receptacle should be able to stay at least partially open in a tert-like structure as shown in FIG. 4.

Figure 5:
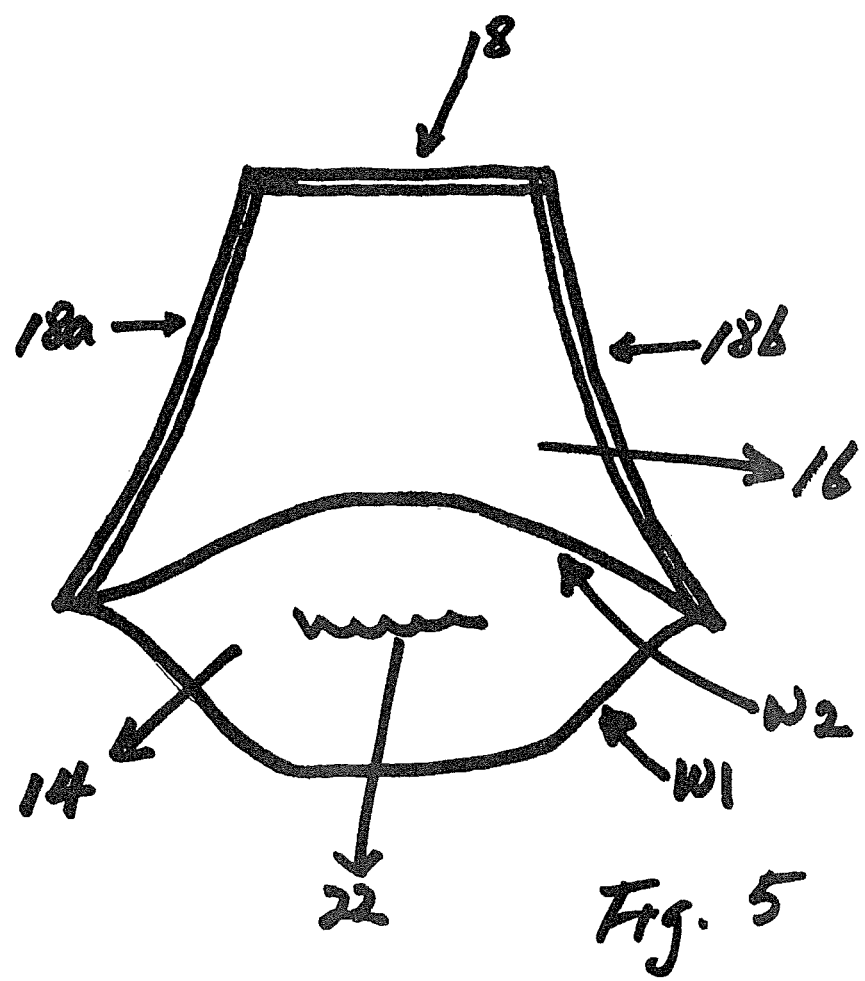
FIG. 5 is a perspective view of a receptacle where the elongate base is wider than the cover

In order to allow the interior area 24 to expand so that one or more medical devices 12 can be inserted therein, the first edge 16a and the second edge 16b flex relative to the elongate base 14 and also flex relative to one another. Additionally, the interior area 24 expands to permit insertion of one or more medical devices 12 when a width W1 of the elongate base 14 is smaller than a width W2 of the cover 16 (FIG. 1). In another embodiment, it is contemplated that the width W1 of elongate base 14 is larger than the width W2 of the cover 16 (FIG. 5).

Figure 1A:
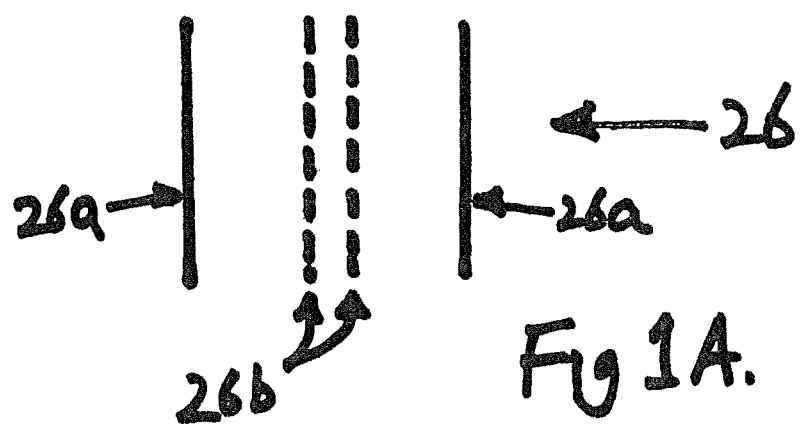
FIG. 1A is an enlarged portion of the receptacle illustrated in FIG. 1.
Figure 1B:
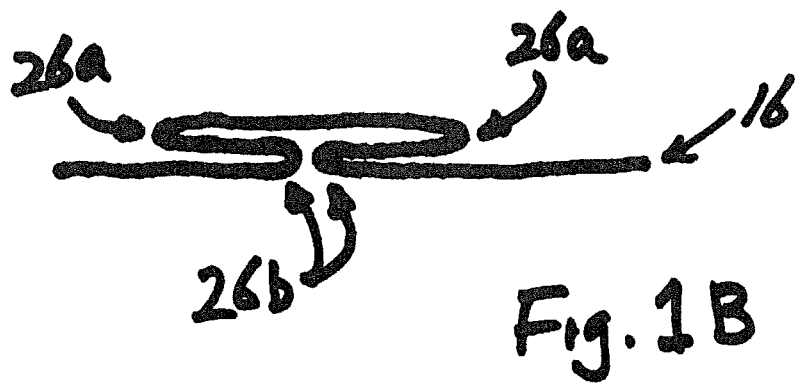
FIG. 1B is a cross-sectional view taken along line B-B of FIG. 1.

As shown in FIG. 1A, the fold 26 may include two outwardly facing folds 26a and two inwardly facing folds 26b. Folds 26, 26a and 26b are, for example, creases in the material used to make the cover 16. While not illustrated, it is contemplated that the fold 26 can have more or less than two outwardly facing folds 26a and more or less than two inwardly facing folds 26b. The outwardly facing folds 26a and the inwardly facing folds 26b are secured in the seam 18. A similar fold configuration may be utilized on the elongate base 14 instead of, or in addition to, the fold configuration on the cover 16.

The biasing member may also be a differential length, i.e., the length of the cover 16 may be shorter than the length of the elongate base 14, as shown in FIG. 1, or vice versa (not shown). The difference in length may further promote the separation of the elongate base 14 from the cover 16 thereby allowing easy insertion of a medical device into the mouth 22 of the receptacle 10.

Figure 7:
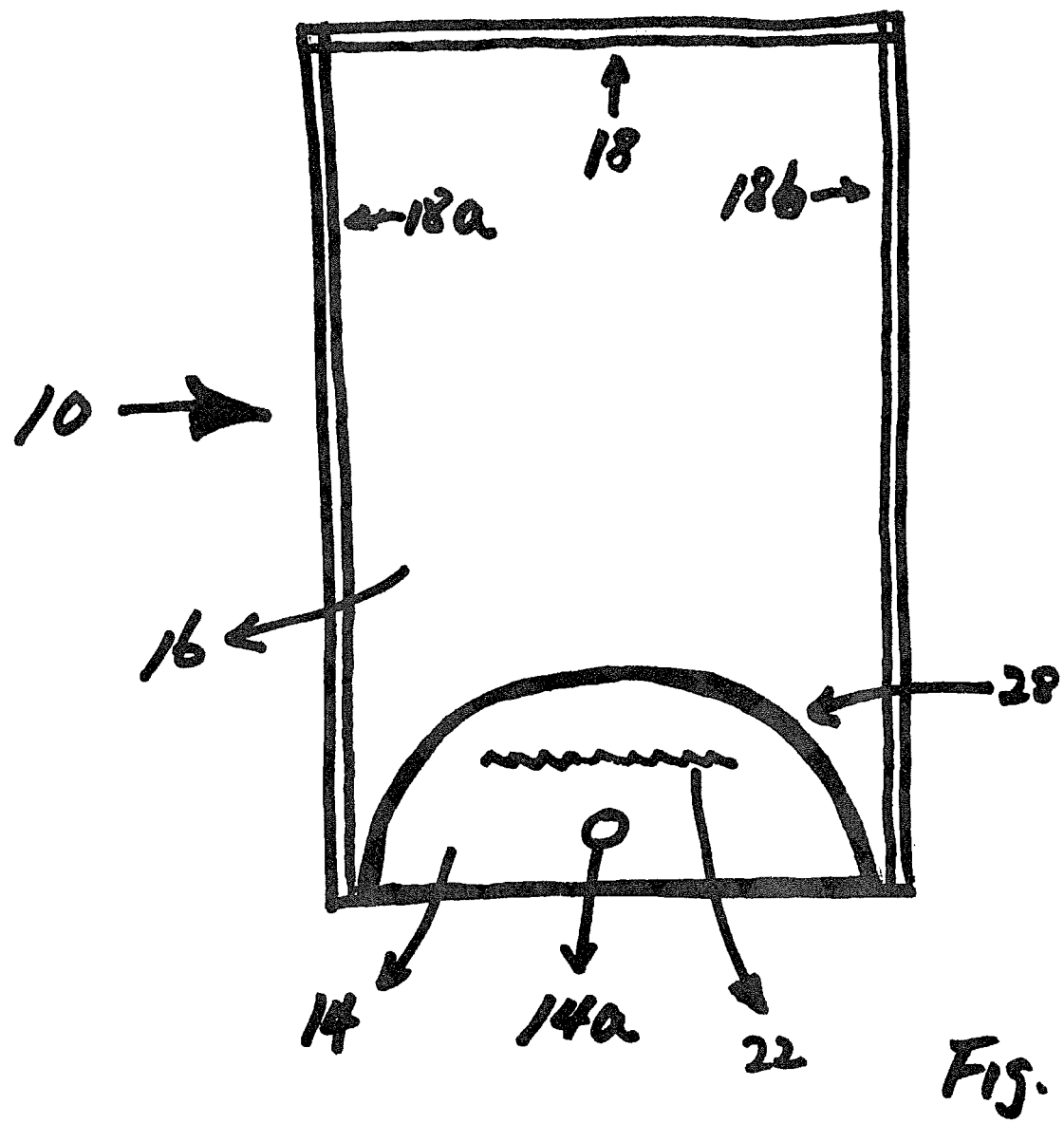
FIG. 7 is a top view of a receptacle according to an embodiment discussed herein.

In another embodiment, as shown in FIG. 7, the mouth 22 has a U-shaped configuration and the biasing member may be an elastomeric ring 28, such as a D-shaped ring, is secured to the mouth 22. FIG. 3 illustrates the mouth 22 of cover 16 having a semi-circular-shaped configuration; however the receptacle 10 is not limited in this regard since the mouth can have any shaped configuration with an elastomeric ring secured thereto. While a D-shaped ring is illustrated in FIG. 7, the ring 28 is not limited in this regard as it may be an O-shaped, or other-shaped ring.

Figure 6:
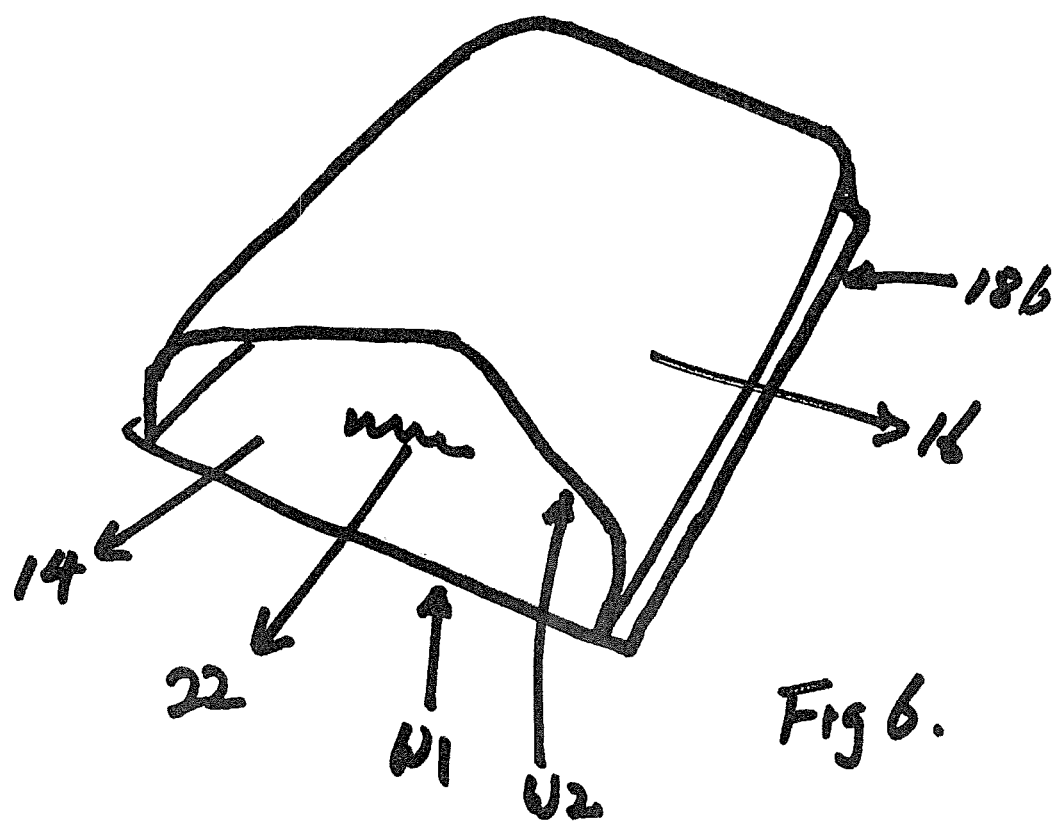
FIG. 6 is a perspective front view of a receptacle having no fold on the cover and an elongate base and cover made of different material.

The receptacle 10 may have no fold on the cover and/or an elongate base 14 and cover 16 made of different material, as shown in FIG. 6. In another embodiment, it is contemplated that the biasing means may simply be the thickness of the material used to make elongate base 14 and the cover 16.

While not illustrated in the drawings, it is contemplated that the mouth 22, or a portion of the mouth, may be distinguished from the other portions of the receptacle 10 in order to promote easy identification of the mouth. For example, the mouth 22 or a portion of the mouth may be a different color than the remainder of the receptacle 10, or have printing thereon. Further examples of distinguishing characteristics for the mouth 22 include but are not limited to having a raised structure, a rolled structure, or a folded structure.

It is contemplated that the biasing member may be any device or mechanism that is configured to bias the mouth 22 in an open position for receiving the medical device 12 through the mouth into the interior area 24. For example, the biasing member may be flexible material, e.g., an elastomer, of any shape that is attached to the mouth 22 or to a portion of the cover 16 facing the elongate base 14.

The dimensions of receptacle 10 can be altered to suit the needs of a user. For example, the receptacle 10 can be made in several different sizes so it can be used in different settings. Some settings may prefer large receptacles 10 to accommodate bulky, large or many medical devices 12 while other settings may prefer smaller receptacles due to space constraints or the use of smaller or fewer medical devices. Accordingly, the size of the receptacle 10 and the size of the cover 16 and elongate base 14 can be varied.

The receptacle 10 may be manufactured by any method known in the art, and the particular apparatus and devices used may vary depending on the size of the receptacle and/or the materials used to make the receptacle. In general, the receptacle 10 is made by hingedly securing the cover 16 and the elongate base 14 such that the cover and the elongate base cooperate to define the envelope 20 having the mouth 22 extending into the interior area 24 of the envelope. After the cover 16 and the elongate base 14 are hingedly secured, a biasing member is positioned to communicate with the cover and to bias the mouth 22 in an open position for receiving the medical device 12 through the mouth into the interior area 24.

Figure 8:
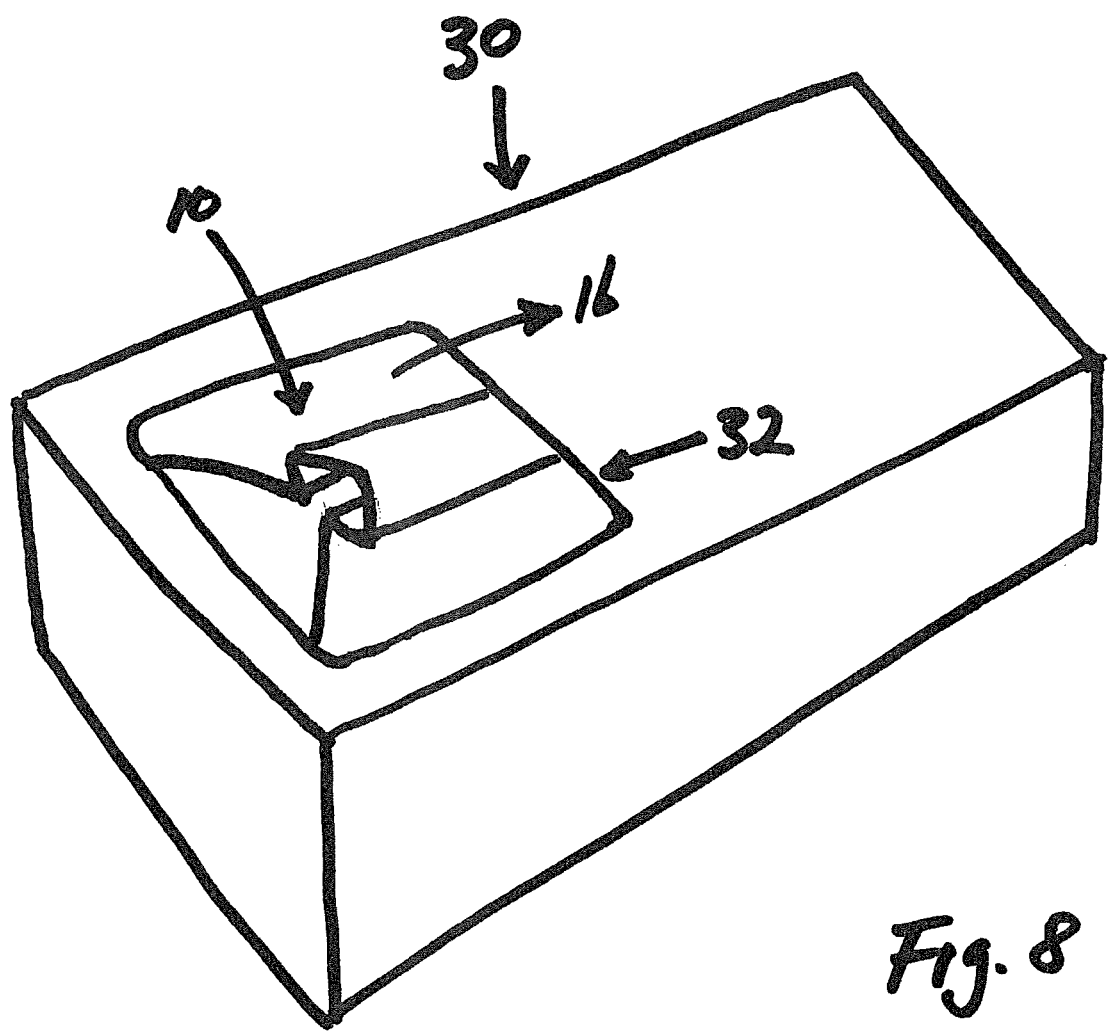
FIG. 8 is a perspective view of a dispenser for dispensing a receptacle as described herein.

Several receptacles 10 may be stored in flattened form stacked atop one another in a dispenser 30 as shown in FIG. 8. The dispenser 30 includes an opening 32 that allows a user to grab a fold 26 of the receptacle 10 and remove the receptacle from the dispenser. Upon removing the receptacle 10 from the dispenser in such a fashion, the mouth 22 is biased in an open position for receiving the medical device 12, i.e., it is deployed for use. The dispenser 30 promotes grabbing the receptacle 10 at a specific portion of the receptacle that promotes easy removal from the dispenser and easy deployment of the receptacle for use.

After the receptacle 10 is dispensed and the mouth 22 is biased in an open position, the receptacle is positioned at a location that is easily accessible to medical personnel, such as a doctor or nurse, while they are monitoring or managing a patient. Such a location may be, for example, on an anesthesia machine, on a cart, on an OR table next to the patient or on a portion of the patient's body, such as the patient's chest or back. In one example, the receptacle 10 may be positioned such that it is fastened, e.g., with tape, to the medical personnel or to a surface 34 such as the top or side of an OR table.

After the receptacle 10 is removed from the dispenser 30, a clean medical device, such as a laryngoscope blade of a laryngoscope, can be stored in the receptacle during a medical procedure in accordance with the present invention. A laryngoscope such as that shown in FIGS. 9-14 consists of a cylindrical handle 12a for gripping by the operator and a removable blade 12b for insertion into the patient's airway, as the patient lies on his or her back, to obtain a view of the vocal folds and the glottis. Blade 12b, which is connected to handle 12a by a hinge 12c which swings approximately 90 degrees, may be inserted into the mouth 22 of the receptacle 10 with the base of the laryngoscope blade resting on base portion 14a and protruding through the mouth 22. The laryngoscope handle 12a can be attached to the base of the blade 12b while holding the blade in the receptacle, thus isolating the clean blade from a handle that is or may potentially be contaminated. Such an arrangement allows for engaging the blade 12b to the handle 12a, testing the assembled handle, checking the light, and storing the assembled laryngoscope in a folded and ready-to-use configuration in the receptacle 10 with the clean blade 12b isolated from the potentially contaminated handle 12a. Additionally, it is noted that once the laryngoscope blade 12b is used on a patient and is therefore contaminated, it can then be inserted into the mouth 22 of the receptacle 10, thereby isolating it from contaminating the handle, other device, equipment or people. The shorter cover 16 length permits the blade 12b to rest on the inner surface of base 14, while the blade base portion hingedly connected to the handle 12a is beyond the end of cover 16, and the remaining portion of the laryngoscope handle 12a rests on top of the upper surface of cover 16.

After a medical device 12 is used on the patient, or otherwise contaminated, the medical device is inserted into the receptacle 10 for disposal or storage. It is contemplated that at least a contaminated portion of the medical device 12 can be stored in the receptacle 10 without contaminating another portion of the medical device, the surrounding environment, people or other medical devices. The medical device 12 is inserted through the mouth 22 to the interior area 24. It is contemplated that the medical device 12 is a disposable device, that is, it is not reusable; however, there may be instances where there are entire medical devices or portions of medical devices that are reusable after cleaning and/or sterilization. In an instance where an entire medical device 12 or a portion of a medical device can be reused, that device or portion is removed from the receptacle 10 before the receptacle is discarded.

Figure 9:
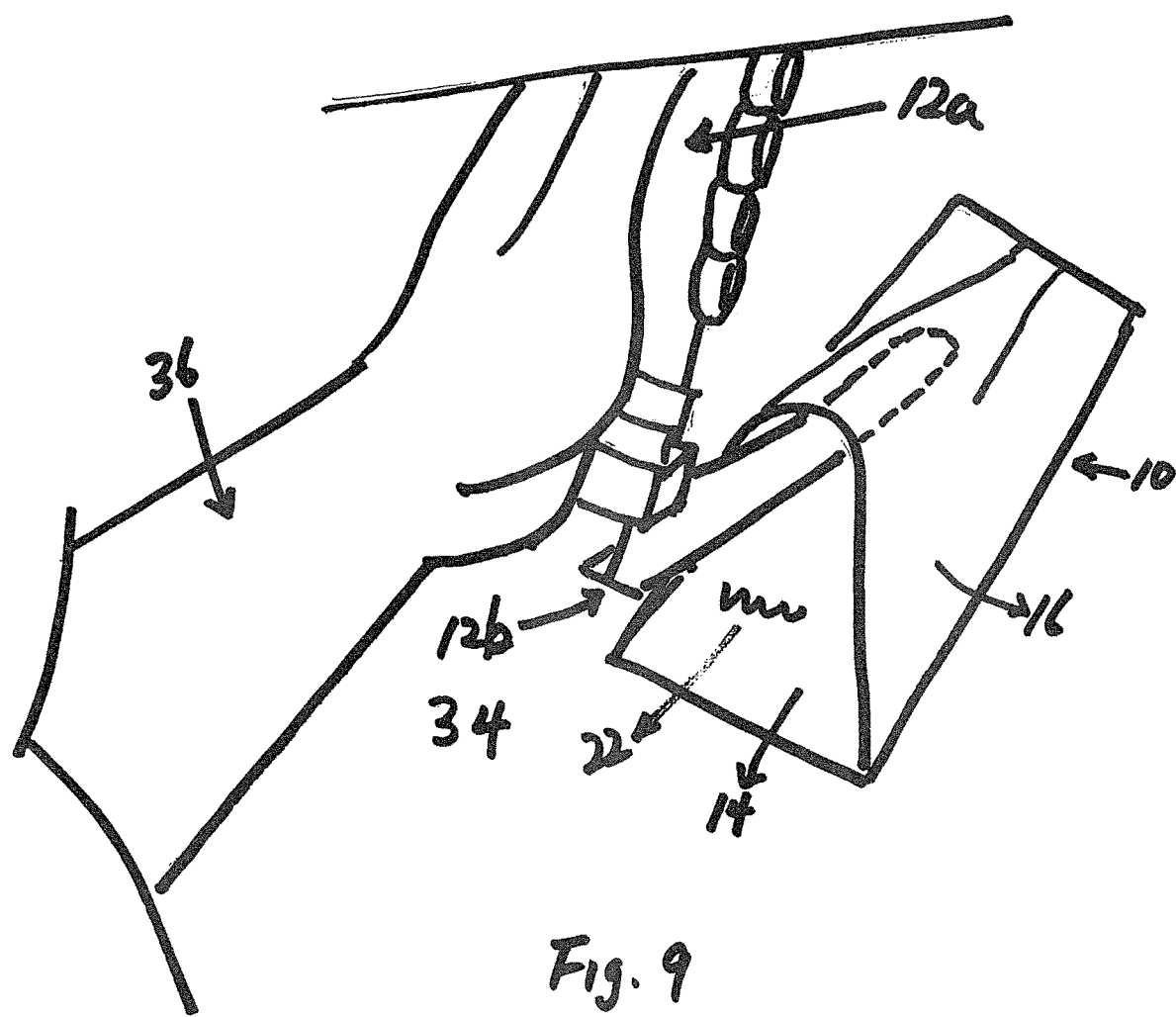
FIG. 9 is a perspective view demonstrating one-handed insertion of a blade of a laryngoscope into a receptacle.
Figure 10:
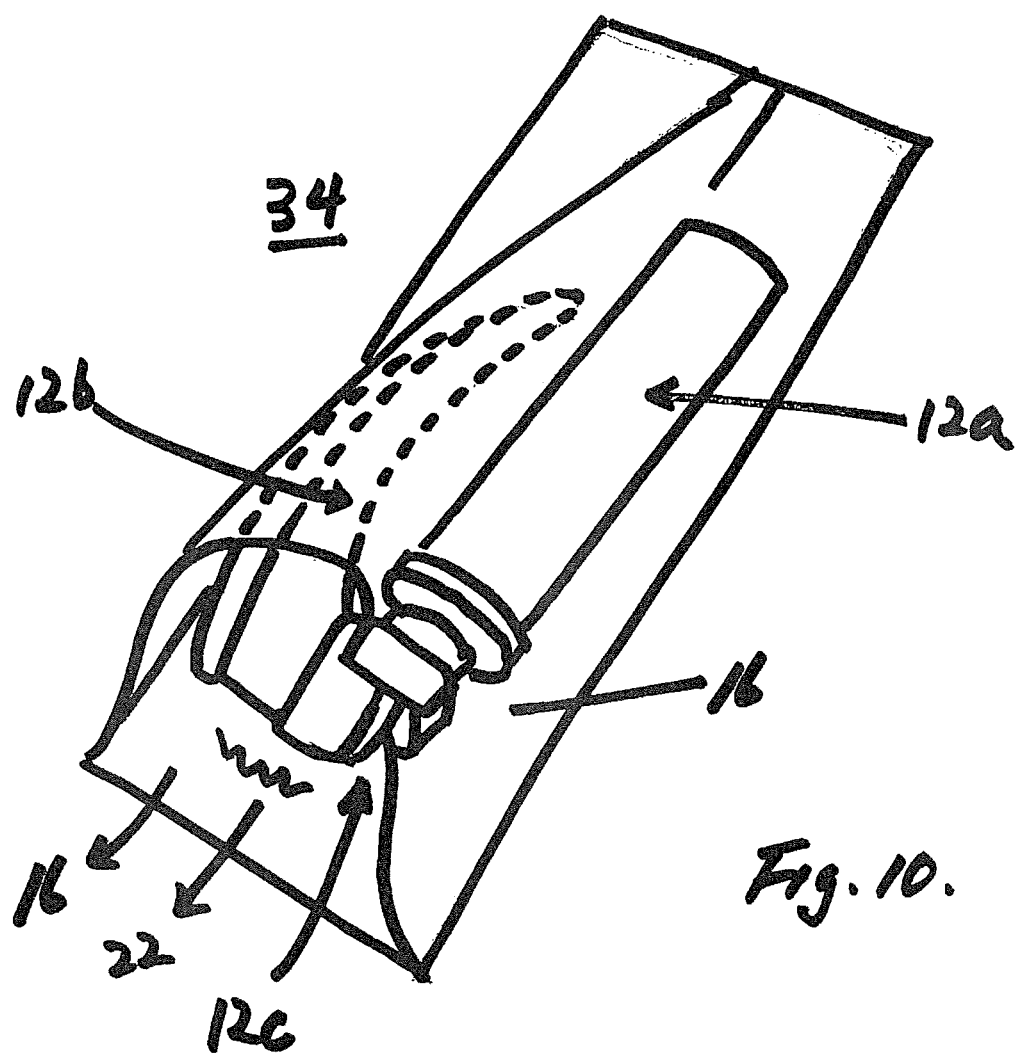
FIG. 10 is a perspective of a receptacle in use storing the laryngoscope blade inside the envelope and the handle resting outside on the cover.

FIGS. 9-14 illustrate use of receptacle 10 to store a laryngoscope blade during surgery or other medical procedure in more detail. Initially, the operator or user may identify the laryngoscope handle and identify the laryngoscope blade still in its original packaging from the manufacturer. The operator may tear an opening on the blade packaging near the blade base and attach the handle to the blade while keeping the body of the blade still inside the packaging. The operator may extend the blade to test the light and proper functioning of the laryngoscope to ensure that it is operable. The operator may then identify the receptacle to be used to store the blade during the medical procedure, which may be the original packaging, or only a portion of the original packaging. If the receptacle is not the original packaging, the operator removes and discards the blade packaging from the laryngoscope. The operator 36 holds the laryngoscope by handle 12a with one hand, inserts the blade part 12b of the laryngoscope into the opening 22 of the receptacle 10 (FIG. 9), and folds the laryngoscope (so that the handle and blade are substantially parallel) to extinguish the laryngoscope light (FIG. 10). As described previously, the receptacle 10 has a base 14 for contact with the surface 34 and an opposite, cover out of contact with the surface. The cover 16 may be shorter than the base 14 at the mouth 22 of the receptacle to facilitate insertion of the blade into the interior of the receptacle and permit the blade 12b to remain isolated and out of contact with the underlying surface when the handle 12a is folded down. The present invention maintains the cleanliness of the blade by ensuring that the blade remains inside the receptacle, and the handle remains outside the receptacle, thus preventing the blade (except the base) from coming in contact with the handle, hands, and the surrounding environment. The receptacle is then positioned on a substantially horizontal surface 34 within easy reach, for example, on the operating table or another table within an arm's reach of the operator while standing or sitting near the patient's head. An adhesive may be provided on the exterior surface of the receptacle base 14 to permit it to be removably secured to the surface to maintain it in the desired position. The laryngoscope is now in standby position ready for use.

Figure 11:
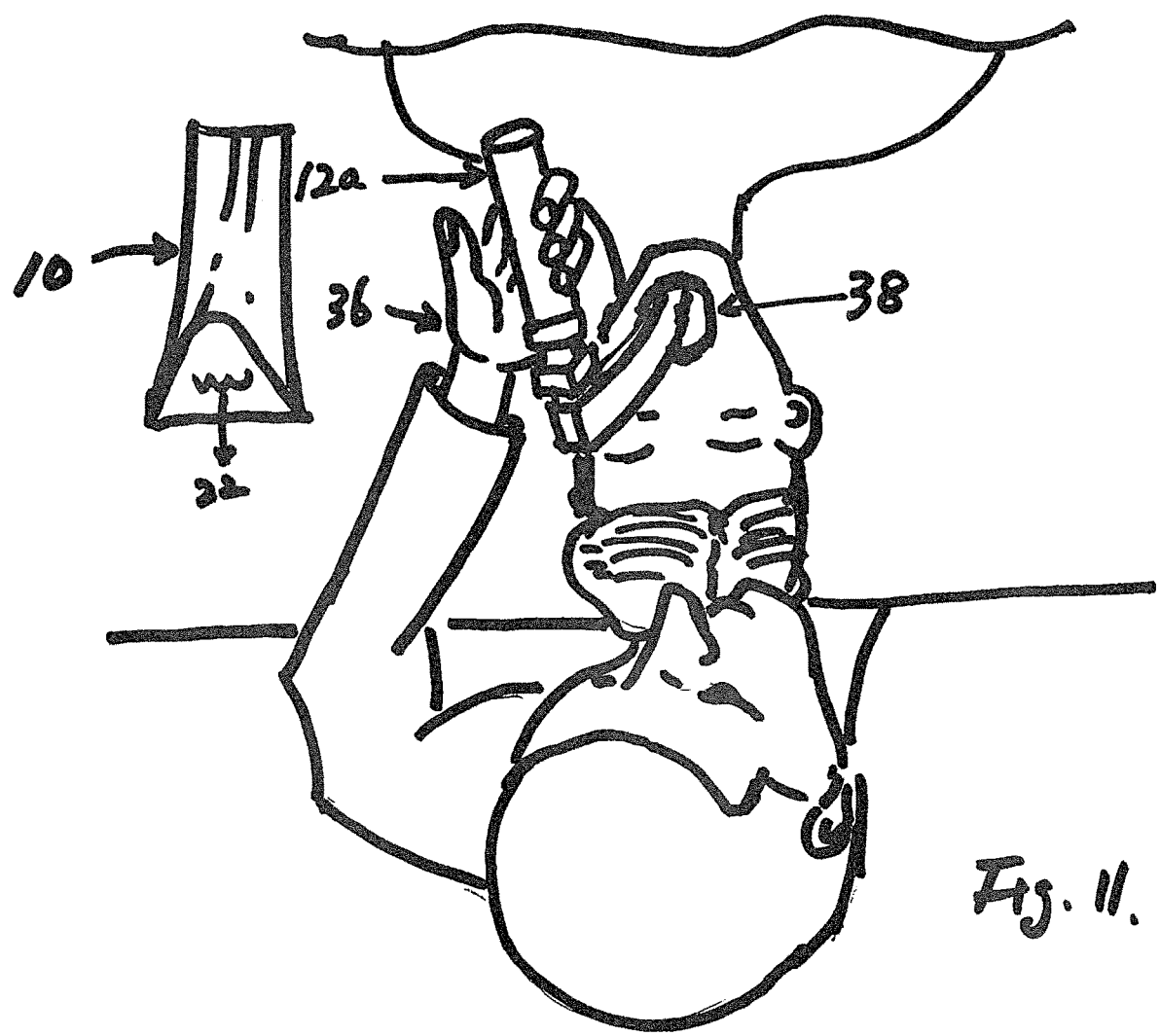
FIG. 11 is a top down perspective view of an operator inserting the laryngoscope blade into the airway of a patient using one hand, with the receptacle of the present invention within arm's reach.
Figure 12:
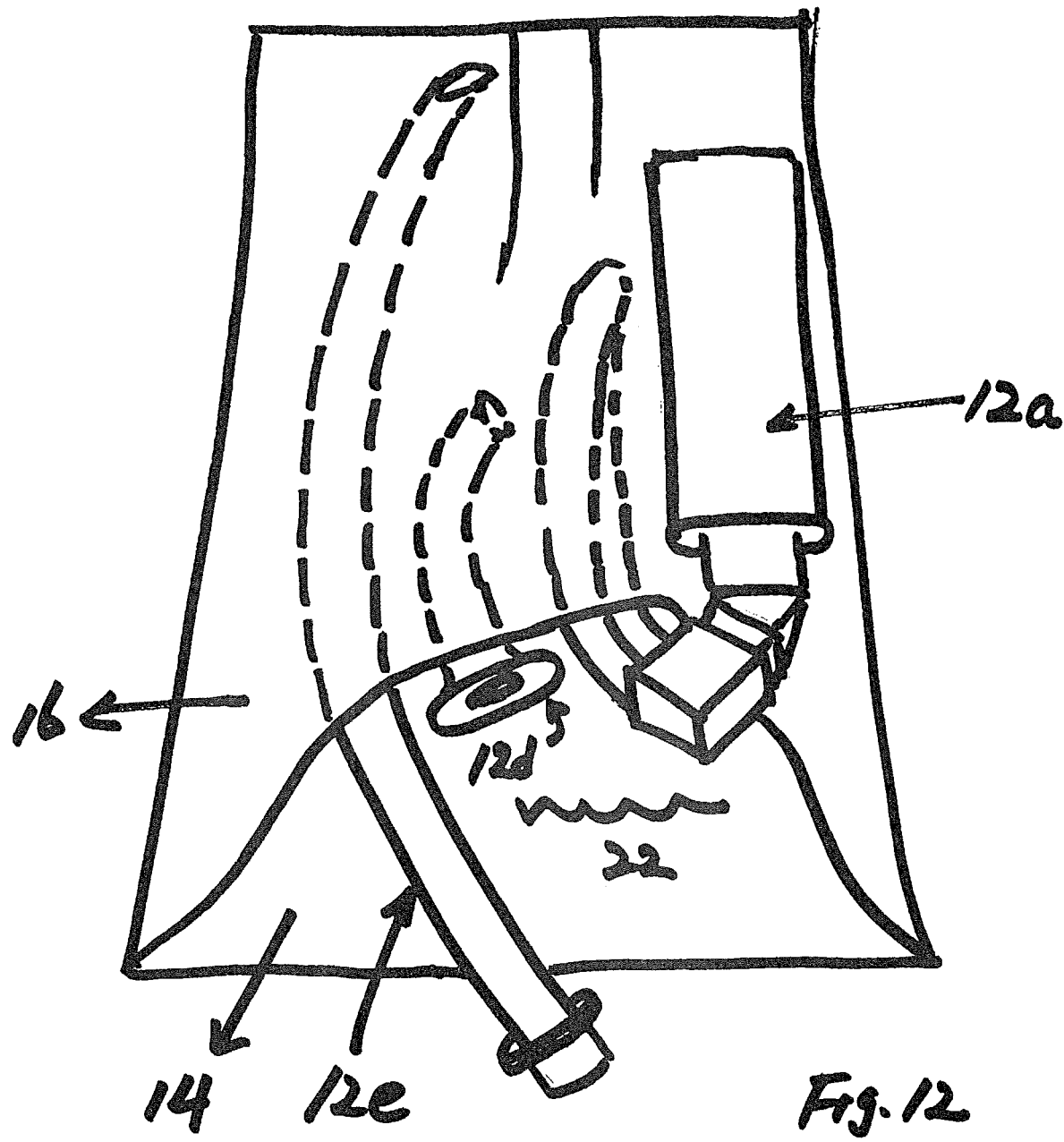
FIG. 12 is a perspective view of a receptacle in use storing several medical devices.
Figure 13:
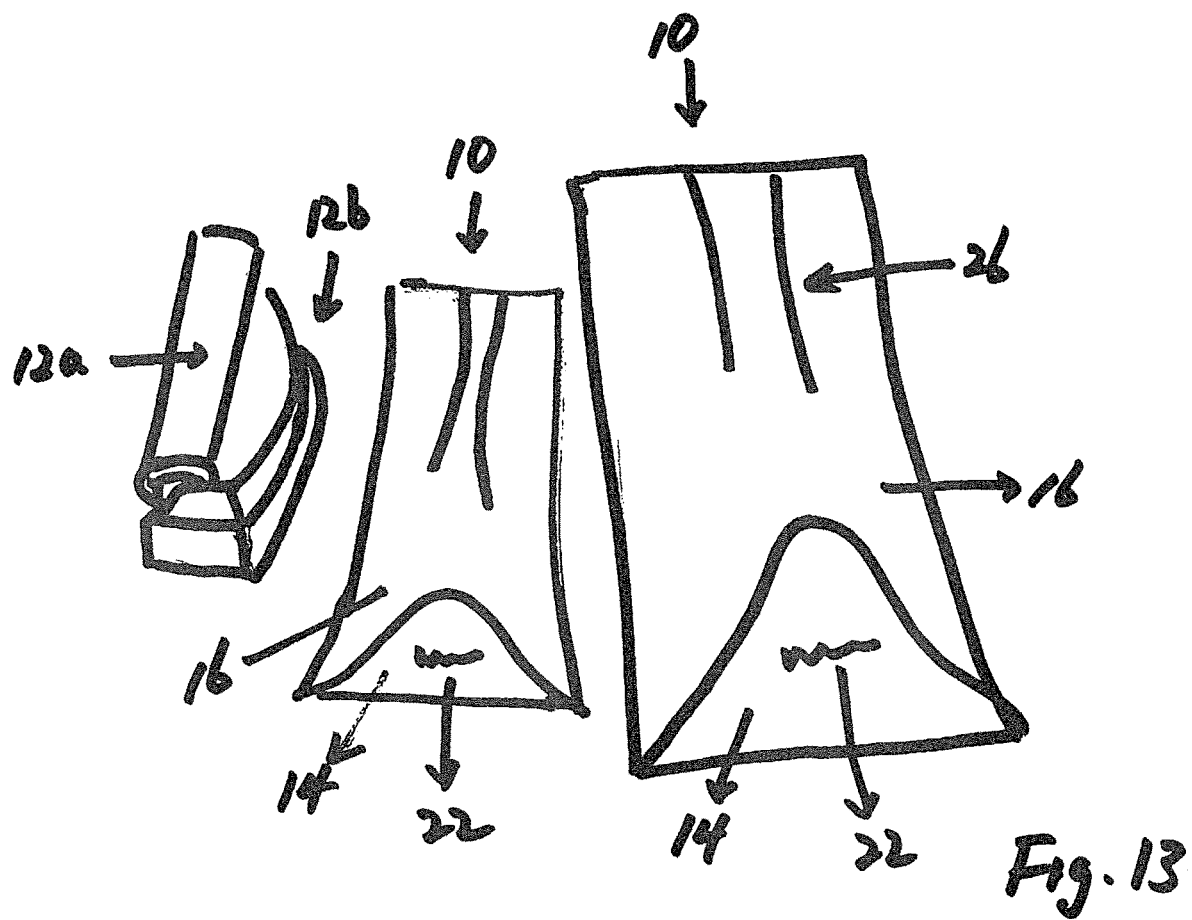
FIG. 13 is a perspective view of two different sized receptacles.
Figure 14:
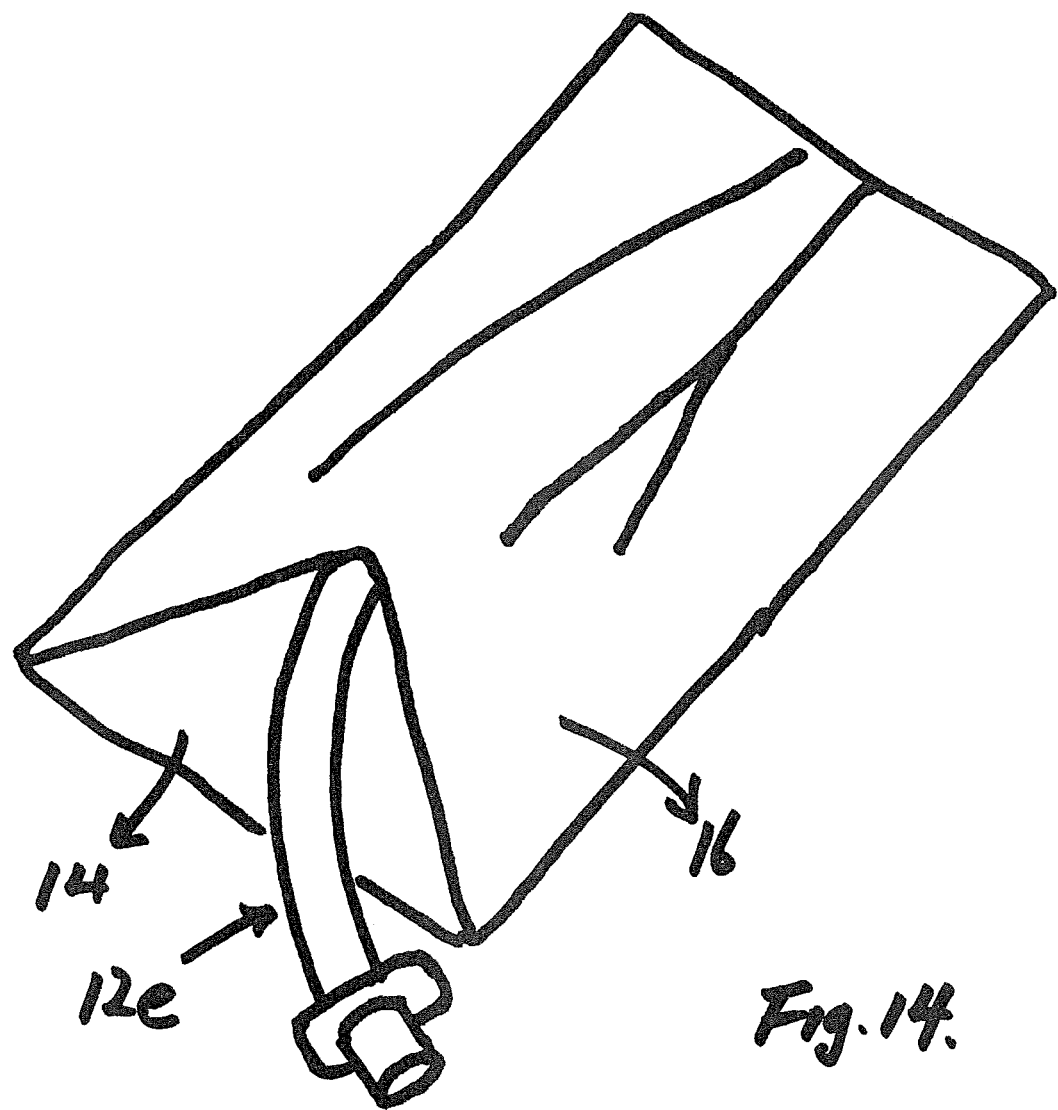
FIG. 14 is a perspective view of a receptacle in use storing an endotracheal tube.

The operator, who is normally a certified medical practitioner, may then prepare for the medical procedure by pre-oxygenating the patient and inducing, i.e., making unconscious, the patient. The operator may mask ventilate the patient and place an oral or nasal airway in the patient as needed to help with mask ventilation. The operator then identifies the laryngoscope stored nearby in standby position with the blade in receptacle 10 and, after the patient is asleep, grasp the handle with one hand, e.g., the left hand, unfolds the handle approximately 90 degrees away from the blade to turn on the light, and removes the laryngoscope from the receptacle (not shown). The now empty receptacle is maintained within easy reach with the mouth 22 of the receptacle in the open position. If an oral airway 12d or nasal airway was previously used, the operator may remove it from the patient and place it into the receptacle 10 (FIG. 12) to prevent contamination of the airway device from the surrounding environment and also to prevent the contamination of the surrounding environment with the device. The operator may then open the patient's mouth with the other hand, e.g., the right hand, while still holding the laryngoscope in the left hand and, using the left hand, insert the blade into patient's oral cavity (FIG. 11). As the left hand maintains its grip on the laryngoscope, the operator may visualize the patient's vocal cords and, using the right hand, insert the endotracheal tube (ETT) 12e (FIG. 12) through the vocal cords until the cuff of the ETT just passes beyond the vocal cords. With the left hand holding the laryngoscope and the right hand holding the ETT, the operator may take note of the depth marking on ETT at teeth.

While maintaining control of the ETT with the right hand, the operator may then remove the blade from the patient's oral cavity and, without releasing grip of the laryngoscope handle 12a and without permitting the blade 12b to contact anything else, insert the substantial part of the blade 12b into the receptacle interior 24 through its opening 22 using the left hand 36 (FIG. 9). Having the opening 22 in a wide open configuration helps with the insertion of the blade 12b, which may now be dripping with the mucus, saliva or blood from the patient's oral cavity into the interior 24 of the receptacle and substantially contain the debris from contaminating the lips of the mouth opening 22, the exterior surface of cover 16, the exterior surface of base 14, the area 34 on which the receptacle is disposed, personnel, other medical equipment, and the surrounding. After inserting the blade into the receptacle, the operator may fold the laryngoscope handle toward the blade while the blade is pushed against the interior surface of the receptacle, so that handle (FIG. 10, 12a) and blade (FIG. 10, 12b) are now collapsed to extinguish the laryngoscope light, and release the handle from the left hand. FIG. 10, laryngoscope stored in collapsed configuration. After releasing the handle 12a the operator ensures that the blade is prevented from coming in contact with the handle, the operator or the surface on which the receptacle is disposed and remains isolated substantially inside the receptacle interior, while the handle remains outside and on the receptacle cover, without the handle touching the surface on which the receptacle is disposed (FIG. 10). This prevents the now soiled blade from contaminating the handle, hands or the surrounding environment and also ensures that the blade does not get contaminated by the handle, hands or the surrounding environment. The operation of storing the laryngoscope may be performed in a one-handed manner, and does not require the use of the operator's other hand. The laryngoscope is then available in temporary storage for reuse later if necessary.

The operator may then continue with the medical procedure and inflate the ETT cuff with a syringe, attach the ventilator to the ETT, ventilate the patient by squeezing the ventilator bag, and ensure that the ETT is in trachea by checking the presence of end tidal CO2 (ETCO2). The operator may subsequently initiate positive pressure ventilation, ascultate patient's lungs, compare the depth marking of the ETT to previously noted depth marking at teeth, and correct any migration of the EH further into or out of the trachea before securing the ETT to the patient, usually with tape. Expeditious confirmation of intubation of the trachea (versus intubation of the esophagus) and prevention of unintended extubation of ETT (therefore the continuous attention to the ETT until it is secured) is of utmost importance and takes precedence over all other activities. The operator may then complete any other urgent patient care tasks. The above activities are some examples of the important patient care tasks that must be accomplished quickly. The medical care provider often lacks the luxury of time or opportunities to dispose of the soiled laryngoscope or other equipment that takes time or attention away from the patient care. The open-mouthed, easy to use configuration of the receptacle in an easy to reach location helps with the containment of the contamination and also allows the operator to do it quickly, with one hand, without taking time or attention away from the patient care where even a momentarily lapse in attention to the patient may result in severe detriment to the patient's wellbeing.

After the immediate patient care needs are met, if not immediately needed, the operator may collect the laryngoscope and the other appliances or devices from the patient area and store them on another location for possible use at a later time. When the laryngoscope and other items stored with the receptacle are no longer needed, the operator may detach the handle from the blade while keeping the blade still inside the receptacle, and discard the blade along with the receptacle in a proper location. If the blade is a reusable type, it can be taken to the processing area while still in the receptacle to prevent contamination of the surrounding environment.

At the conclusion of the surgery, a new or additional receptacle can be placed within easy reach with the mouth of the receptacle in an open position. When the patient is ready for extubation, the ETT can be removed from the patient and placed into the receptacle. The soiled ETT 12e, often dripping with mucus, saliva and blood, can be inserted into and contained within the receptacle 10 without allowing the debris from the distal end of ETT to come in contact with the lips of the opening of the receptacle, exterior surfaces of the receptacle, the surface on which the receptacle is disposed, or the operator. The wide open-mouth configuration and placement of the receptacle provide minimal chance of soiling the lips of the opening or the exterior surfaces of the receptacle and permits the ETT to be inserted into the receptacle with little attention to and with minimal manipulation of the receptacle by the operator. This prevents contamination of the surrounding environment and permits proper disposal as time permits. (FIG. 14) Having the receptacle available within easy reach and in an easy to use configuration enables the operator to quickly and properly dispose of the soiled ETT without having to take attention away from the patient or even look away from the patient during the critical time of emergence when catastrophic events such as vomiting, aspiration, and airway obstruction are most likely to occur.

Another aspect of the invention is directed to medical devices such as laryngoscope blades pre-packaged into the receptacle 10. In such an embodiment, the receptacle 10 includes a perforation, pre-cut, thinned-out, or otherwise modified or weakened area to achieve the opening 22 as described above by simple removal or manipulation, e.g., tearing off, pulling part, and the like. Such removal would allow deployment of the receptacle 10 for use as described above.

A further aspect of the invention is to fold the wider portion of the receptacle 10, either the elongate base 14 or the cover 16, in such a way as to achieve a flat configuration of the receptacle. Such flat configuration is further enhanced by sealing or constructing the non-opening end to promote a low profile and allowing a propagation of such fold or profile to extend to the end of the receptacle 10 having the opening 22.

While a laryngoscope is mentioned in the instant application, the present invention is not limited to a receptacle holding such a medical device. Indeed, any device or item, clean or contaminated, may be placed in the receptacle 10. Other particular examples of medical devices include, but are not limited to, oral airway, nasal airway, tongue depressor, suction catheter, Glidescope blade, other intubation devices and endotracheal tubes. The receptacle may be used to hold any device or item, medical or non-medical.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A receptacle for receiving a medical device, the receptacle comprising:
    an elongate base having a first end and a second opposite end; and
    a cover hingedly secured to the elongate base adjacent to the second end, the cover and the elongate base cooperating to define an envelope having a mouth arranged adjacent to the first end and extending into an interior area of the envelope, wherein an axial length of the base at the mouth is longer than an axial length of the cover at the mouth, and the axial length of the cover gradually increases from a center of the cover towards an opposing first edge and second edge of the cover;
    wherein the mouth is biased in a normally-open position for receiving at least a portion of the medical device through the mouth into the interior area.

2. The receptacle of claim 1, including a biasing member communicating with the cover and configured to bias the mouth in the normally-open position.

3. The receptacle of claim 2, wherein the biasing member is defined by at least one fold in the cover.

4. The receptacle of claim 3, wherein the at least one fold includes two outwardly facing folds and two inwardly facing folds.

5. The receptacle of claim 4, wherein the cover is hingedly secured to the base at a seam, and at least one fold is secured in the seam and fans progressively outward toward the mouth.

6. The receptacle of claim 3, wherein the cover includes a first edge and a second edge and the at least one fold is positioned between the first edge and the second edge.

7. The receptacle of claim 6, wherein the first edge and the second edge flex relative to the elongate base and relative to one another to expand the interior area.

8. The receptacle of claim 2, wherein the elongate base and the cover are hingedly secured to one another by a seam therebetween.

9. The receptacle of claim 2, wherein the biasing member is the cover which is wider than the base.

10. The receptacle of claim 2, wherein the biasing member is defined by one or more folds in at least one of the cover and the elongate base.

11. The receptacle of claim 1, wherein the mouth has a V-shaped configuration.

12. The receptacle of claim 1, wherein the elongate base and the cover comprise a polymeric material.

13. A receptacle for receiving a medical device, the receptacle comprising:
    an elongate base having a first end and a second end; and
    a cover distinct from the elongate base, the cover being hingedly secured to the elongate base at the second end, the cover and the elongate base cooperating to define an envelope having a mouth extending into an interior area of the envelope, the cover having a first edge and a second opposite edge and an axial length at least one of the first edge and the second edge being substantially equal to an axial length of the base, wherein a length of at least a portion of the cover at the mouth is less than a length of the elongate base at the mouth such that when the cover is flattened against the elongate base, an upper surface of the elongate base is exposed at the mouth;

wherein the mouth is biased into a normally-open position for receiving at least a portion of the medical device through the mouth into the interior area.

14. A receptacle for receiving a medical device, the receptacle comprising:
   an elongate base having a first end and a second opposite end; and
   a cover hingedly secured to the elongate base adjacent to the second end, the cover and the elongate base cooperating to define an envelope having a mouth, wherein an axial length of the base at the mouth is longer than an axial length of the cover at the mouth; and
   at least one fold formed in the cover, wherein the mouth of the envelope is biased into an open position, via the at least one fold, for receiving at least a portion of the medical device within an interior area of the envelope, the at least one fold including two outwardly facing folds positioned adjacent to one another near a center of the cover.

15. The receptacle of claim 14, wherein the cover includes a first edge and a second edge and the at least one fold extends substantially parallel to at least one of the first edge and the second edge.

\* \* \* \* \*